United States Patent
Harada et al.

(10) Patent No.: US 6,524,999 B2
(45) Date of Patent: Feb. 25, 2003

(54) GROWTH INHIBITORS AGAINST ALGAE AND MOSS

(75) Inventors: Satoshi Harada, Tochigi (JP); Hideyoshi Toyoda, Tochigi (JP)

(73) Assignee: Kagome Kabushiki Kaisha, Aichi (JP)

(*) Notice: Subject to any disclaimer, the term of this patent is extended or adjusted under 35 U.S.C. 154(b) by 0 days.

(21) Appl. No.: 09/894,211

(22) Filed: Jun. 27, 2001

(65) Prior Publication Data

US 2002/0037812 A1 Mar. 28, 2002

(30) Foreign Application Priority Data

Jun. 27, 2000 (JP) ......................................... 2000-192591

(51) Int. Cl.$^7$ ............................................. A01N 43/38

(52) U.S. Cl. ..................................................... 504/158

(58) Field of Search ................................ 504/283, 158; 548/494

(56) References Cited

PUBLICATIONS

Matusuda et al. "Control of the Bacterial Wilt of Tomato Plants by a Derivative of 3–Indolepropionic Acid Based on Selective Actions on Ralstonia solanacearum". J. Agric. Food Chem. 46:4416–4419. 1998.*

Moore, Thomas C. Biochemistry and Physiology of Plant Hormones. NY:Springer–Verlag. p. 37–39. 1979.*

Marumo, Shingo. "Auxins", Chapter 2 in Chemistry of Plant Hormones, Nobutaka Takahashi, ed. Boca Raton, FL:CRC Pr. p. 16–26. 1986.*

* cited by examiner

Primary Examiner—S. Mark Clardy
(74) Attorney, Agent, or Firm—Beyer Weaver & Thomas LLP

(57) ABSTRACT

Growth inhibitors containing 3-(3-indolyl) butyric acid shown by

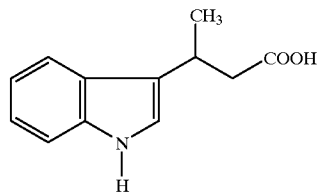

and its salts can prevent the growth of algae and moss without harming the plants being cultivated or the worker or adversely affecting the environment.

3 Claims, No Drawings

GROWTH INHIBITORS AGAINST ALGAE AND MOSS

BACKGROUND OF THE INVENTION

This invention relates to growth inhibitors against algae and moss. In hydroponic culture of plants in a greenhouse environment, a growth of algae and moss is usually observed in the nutrient solution itself or on the machines and devices which come into contact with the nutrient solution. Such algae and moss tend to clog these machines and devices, preventing the nutrient solution from being circulated smoothly. When saplings of a plant such as lawn are grown, too, algae and moss are often seen to grow in the soil or on their supports. Such algae and moss not only adversely affect the external appearance of the plants but also cause a bad odor. The present invention relates to chemicals which are capable of inhibiting the growth of such undesirable algae and moss.

Copper sulfate, hydrated lime, agricultural chemicals and quaternary ammonium compounds have been known as growth inhibitors against algae and moss, and it has also been known that indoleacetic acid and 3-indole propionic acid have some functions of inhibiting the growth of algae and moss. Copper sulfate and hydrated lime, however, are harmful to the plants themselves, although this depends on the amount to be used, while agricultural chemicals and quaternary ammonium compounds tend to be harmful to the user as well as to the environment. As for indoleacetic acid and 3-indole propionic acid, they are not significantly effective as a growth inhibitor.

SUMMARY OF THE INVENTION

It is therefore an object of this invention to provide chemicals which are not harmful to plants themselves, have not harmful effects on workers and the environment but are capable of sufficiently inhibiting the growth of algae and moss even if only a small amount is used.

The invention is based on the discovery by the present inventors as a result of their diligent investigations in view of such an object that 3-(3-indolyl) butyric acid and its salts are appropriate growth inhibitors against algae and moss.

DETAILED DESCRIPTION OF THE INVENTION

This invention relates to growth inhibitors against algae and moss containing 3-(3-indolyl) butyric acid as shown by Formula 1 given below or its salt as an effective component:

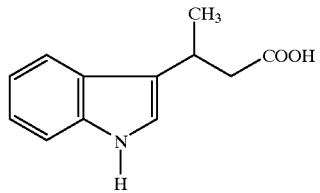

(Formula 1)

Examples of salt of 3-(3-indolyl) butyric acid shown by Formula 1 include alkali metal salts such as sodium and potassium salts, alkali earth metal salts such as calcium and magnesium salts and ammonium salt.

As will be explained more in detail below, 3-(3-indolyl) butyric acid and its salts can inhibit the growth of algae and moss sufficiently effectively even with a small amount.

The following two kinds of growth inhibitors may be presented as embodying this invention: (1) growth inhibitors against algae and moss containing 3-(3-indolyl) butyric acid as shown by Formula 1 as effective component; and (2) growth inhibitors against algae and moss containing potassium salt of 3-(3-indolyl) butyric acid as shown by Formula 1 as effective component.

The invention will be described next by way of test examples.

Test Examples
Part 1
Synthesis of 3-(3-indolyl) butyric acid shown by Formula 1

Indole 3 g and Meldrum's acid 4.43 g were dissolved in 30 ml of acetonitrile and caused to react for 6 hours at 30° C. with stirring by adding 3 ml of acetoaldehyde, refined by distillation immediately before, both at the beginning of the reaction and 2 hours thereafter. After the reaction liquid was concentrated under a reduced pressure condition, it was dissolved in a mixed solvent of 30 ml of pyridine and 3 ml of ethanol, and 150 ml of copper powder was added thereto for a reaction for 6 hours in reflux with boiling. After the reaction liquid was filtered and the pH of the filtered liquid was made acidic by using 2N hydrochloric acid, ether was used for an extraction. After the extracted liquid was washed with water and dried with anhydrous magnesium sulfate, the solvent was removed by distillation under a reduced pressure condition. The residue was refined by means of a silica gel column chromatograph (the gel being Wakogel C-200 (tradename) of Wako Pure Chemical Industries, Ltd., and the solvent being a mixture of hexane and ethyl acetate at ratio of 5/1) to obtain 2.25 g of ethyl ester of 3-(3-indolyl) butyric acid. To this was added 20 ml of a liquid mixture of ethanol and 10% aqueous solution of potassium hydroxide at ratio of 1/1 and an evaporator was used after 6 hours of reflux to obtain a hardened object. Water was added to this hardened object and it was washed with ether. After active charcoal was further added for bleaching with heating, the active charcoal was removed by filtering. The solution was made acidic by adding 2N hydrochloric acid to the bleached liquid to obtain 1.85 g of crystal of 3-(3-indolyl) butyric acid shown by Formula 1.

Part 2
(Hydroponic Culture Test No. 1)

Algae which grew in hydroponic culture of tomato plants inside a greenhouse provided with a hydroponic culture system were collected. A control nutrient solution was prepared by dissolving in 1 liter of water 0.625 g, 0.417 g, 0.042 g and 0.029 g respectively of Otsuka House Nos. 1, 2, 3 and 5 (tradenames of products by Otsuka Chemical Co., Ltd.) Identified in the collected algae were the following nine kinds: Chlamydomonas, Scenedesumus, Actinastrum, Ulothrix, Oscillatoria, Spirogyra, Pleurotaenium, Stichoccus and Chlorella.

The algae thus collected were filtered by using a filtering net with opening diameter of 53 μm. After the filtrate was buried inside the aforementioned control nutrient solution containing agar by 0.8 weight %, disks were cut out therefrom by means of a cork borer. Test nutrient solutions which were individually prepared by adding indoleacetic acid, 3-indole propionic acid or 3-(3-indolyl) butyric acid shown by Formula 1 at different concentrations to the control nutrient solution, and after these disks were immersed individually in these test nutrient solutions for 7 days at 250° C. under a continuous illumination of light at 2500 lux, the growth of algae was visually examined. The result of the observation is shown in Table 1 below.

TABLE 1

| | Concentration (mg/liter) | | | | | | | |
|---|---|---|---|---|---|---|---|---|
| | 0 | 0.1 | 0.5 | 1 | 5 | 10 | 25 | 50 |
| IAA | + | + | + | + | + | + | + | + |
| IPA | + | + | + | + | + | + | + | + |
| IBA | + | + | + | + | + | − | − | − |

In Table 1:
IAA: Test nutrient solution with indoleacetic acid
IPA: Test nutrient solution with 3-indole propionic acid
IBA: Test nutrient solution with 3-(3-indolyl) butyric acid shown by Formula 1
+: Algae growth was clearly observed
−: Algae growth was not observed Part 3:
(Hydroponic Culture Test No. 2)

In hydroponic culture of tomato plants inside a greenhouse provided with a hydroponic culture system, use as nutrient solution was made both of the control nutrient solution prepared in Test No. 1 and Test nutrient solution A obtained by adding 10 mg of 3-(3-indolyl) butyric acid shown by Formula 1 to 1 liter of this control nutrient solution. The plants were grown while these solutions were appropriately supplied under the conditions of about 15° C. at night and about 25° C. during the day, and the growth of algae and moss in the solution and the machines and devices contacting the solution as well as the growth of the tomato plants was visually observed. The results are shown in Table 2 below.

TABLE 2

| | Growth of algae and moss | | | | | Growth of tomato plants | | |
|---|---|---|---|---|---|---|---|---|
| | 4 days | 7 days | 10 days | 14 days | 21 days | 7 days | 14 days | 21 days |
| Cont | + | + + | + + | + + | + + | Good | Good | Good |
| Test A | − | − | − | − | ± | Good | Good | Good |

In Table 2 (and also in subsequent Tables):
Cont: Control nutrient solution
A: Test nutrient solution A
−: Growth of algae and moss not observed
±: Growth of algae and moss slightly observed
+: Growth of algae and moss clearly observed
+ +: Growth of algae and moss significantly observed Part 4
(Hydroponic Culture Test No. 3)

Bentgrass seeds were sown on blocks of rockwool immersed in a control nutrient liquid inside a greenhouse provided with a hydroponic culture system. The control nutrient solution used in Part 4 was prepared by dissolving 1 g of Hyponex (tradename for product by Hyponex Company, Ltd.) in 1 liter of water. Use was also made of Test nutrient solution B ("Test B") prepared by adding 10 mg of 3-(3-indolyl) butyric acid shown by Formula 1 to 1 liter of this control nutrient solution and Test nutrient solution C ("Test C") prepared by adding 25mg of 3-(3-indolyl) butyric acid shown by Formula 1 to 1 liter of this control nutrient solution. Cultivation was carried out while these solutions were appropriately supplied under the conditions of about 15° C. at night and about 30° C. during the day, and the growth of algae and moss in the solution and on the blocks of rockwool as well as the growth of the bentgrass was visually observed. The results are shown in Table 3 below.

TABLE 3

| | Growth of algae and moss | | | | | Growth of tomato plants | | |
|---|---|---|---|---|---|---|---|---|
| | 4 days | 7 days | 10 days | 14 days | 21 days | 7 days | 14 days | 21 days |
| Cont | + | + + | + + | + + | + + | Good | Good | Good |
| Test B | − | − | ± | ± | + | Good | Good | Good |
| Test C | − | − | − | − | ± | Good | Good | Good |

Part 5
(Hydroponic Culture Test No. 4)

Bentgrass seeds were sown on blocks of rockwool immersed in the same control nutrient solution as used in Part 4 inside a greenhouse provided with a hydroponic culture system. Use was also made of Test nutrient solution R ("Test R") prepared by adding 20 mg of indoleacetic acid to 1 liter of this control nutrient solution and Test nutrient solution D ("Test D") prepared by adding 20 mg of 3-(3-indolyl) butyric acid shown by Formula 1 to 1 liter of this control nutrient solution. The hydroponic culture process was carried out while these solutions were appropriately supplied under the conditions of about 15° C. at night and about 30° C. during the day, and the growth of algae and moss in the solution and on the blocks of rockwool as well as the growth of the bentgrass was visually observed. The results are shown in Table 4 below.

TABLE 4

|  | Growth of algae and moss | | | | |
| --- | --- | --- | --- | --- | --- |
|  | 4 days | 7 days | 10 days | 14 days | 21 days |
| Cont | + | ++ | ++ | ++ | ++ |
| Test R | ± | + | ++ | ++ | ++ |
| Test D | − | − | − | − | ± |

As can be understood clearly from these results, the present invention makes it possible to inhibit the growth of algae and moss without harming the target plants to be grown themselves or the workers and without adversely affecting the environment by using only a small quantity of an inhibitor chemical.

What is claimed is:

1. A method of inhibiting algae and moss, comprising applying to said algae and moss a growth inhibitor containing 3-(3-indolyl) butyric acid as shown by

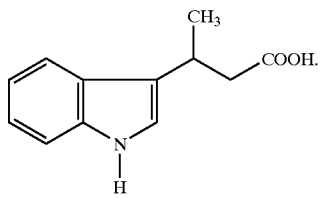

2. The method of claim 1 comprising applying to said algae and moss a salt of said 3-(3-indolyl) butyric acid.

3. The method of claim 2 wherein said salt is a potassium salt.

* * * * *